United States Patent
Månsson et al.

(10) Patent No.: US 7,089,812 B2
(45) Date of Patent: Aug. 15, 2006

(54) TRANSFER OF A SAMPLE FROM A SOLID SUPPORT INTO A LIQUID

(75) Inventors: Per Månsson, Sollentuna (SE); Jan Smith, Enskede (SE); Ann-Charlotte Hellgren, Lidingö (SE)

(73) Assignee: Biosensor Applications Sweden AB, Sundbyberg (SE)

( * ) Notice: Subject to any disclaimer, the term of this patent is extended or adjusted under 35 U.S.C. 154(b) by 33 days.

(21) Appl. No.: 10/495,115

(22) PCT Filed: Nov. 19, 2002

(86) PCT No.: PCT/SE02/02098

§ 371 (c)(1),
(2), (4) Date: May 19, 2004

(87) PCT Pub. No.: WO03/044487

PCT Pub. Date: May 30, 2003

(65) Prior Publication Data

US 2005/0016300 A1  Jan. 27, 2005

Related U.S. Application Data

(60) Provisional application No. 60/331,511, filed on Nov. 19, 2001.

(51) Int. Cl.
*G01N 1/40* (2006.01)

(52) U.S. Cl. .................. 73/864.82; 73/863.11; 73/863.21; 73/864.81; 73/864.83

(58) Field of Classification Search .............. 73/863, 73/863.11, 863.12, 863.21, 863.23, 864, 864.81–864.85, 73/864.91
See application file for complete search history.

(56) References Cited

U.S. PATENT DOCUMENTS

| | | | | |
|---|---|---|---|---|
| RE30,391 E | * | 9/1980 | Liston | 356/409 |
| 4,819,477 A | | 4/1989 | Fisher et al. | 73/28.01 |
| 5,270,211 A | * | 12/1993 | Kelln et al. | 436/43 |
| 5,398,556 A | * | 3/1995 | Lang | 73/863.11 |
| 5,442,175 A | | 8/1995 | Dawson | 250/288 |
| 5,569,837 A | * | 10/1996 | Hinaga | 73/19.01 |
| 6,053,059 A | | 4/2000 | Muranaka et al. | 73/863.12 |
| 6,116,100 A | * | 9/2000 | Jehan | 73/864.81 |
| 6,125,687 A | | 10/2000 | McClelland et al. | 73/19.01 |

\* cited by examiner

FOREIGN PATENT DOCUMENTS

WO  9857141 A1  12/1998

*Primary Examiner*—Hezron Williams
*Assistant Examiner*—David A. Rogers
(74) *Attorney, Agent, or Firm*—Bacon & Thomas, PLLC

(57) ABSTRACT

An apparatus (10) and a method for concentrating and transferring volatile compounds contained in a sample on a detachable solid support (12) into a liquid for subsequent detection and/or analysis of the volatile compounds, are described. The apparatus comprises a holder (14) for the solid support (12), means (16) for transporting the holder (14) to a heating position on a heatable plate (18), an enclosed space-creating arrangement comprising the heatable plate (18) attached to a movable housing (30), the holder (14), the solid support (12), a funnel (20) on the solid support (12), and inside the funnel (20) a chilled member (22), means inside the housing (30) for heating the heatable plate (18) to evaporate the volatile compounds which then are condensed on the chilled member (22), means (24) for transporting the chilled member (22) from a cooler (26) to the inside of the funnel (20) and from there to a position (28) where condensed compounds are removed from the chilled member (22) into a liquid.

4 Claims, 1 Drawing Sheet

TRANSFER OF A SAMPLE FROM A SOLID SUPPORT INTO A LIQUID

Figure 1:
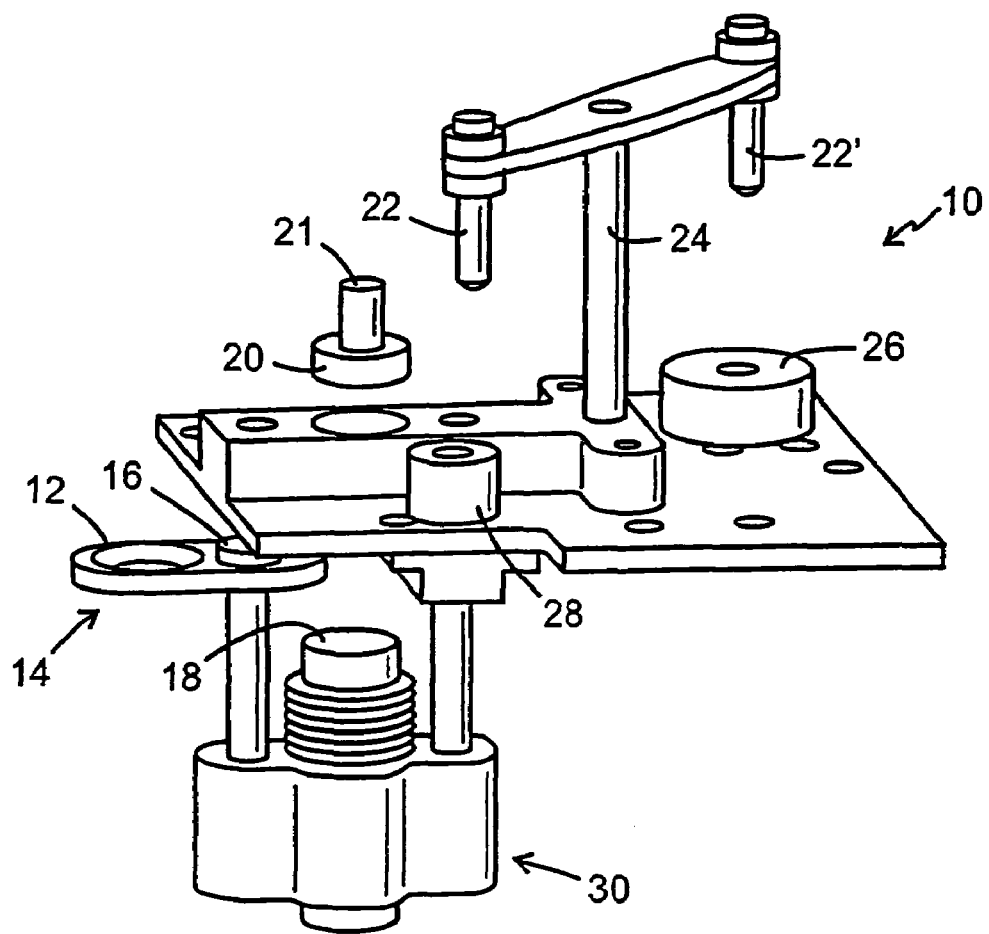

This application is a 371 of PCT/SE02/02098, filed Nov. 19, 2002, which claims benefit of priority from U.S. Provisional Application 60/331,511, filed Nov. 19, 2001.

The present invention relates to transfer of a sample, or more precisely volatile compounds contained in the sample, from a solid support into a liquid. The invention is particularly concerned with a method and apparatus for transferring volatile compounds contained in a sample placed on a solid support into a liquid for detection and/or analysis of one or several of the volatile compounds.

BACKGROUND

In the development of apparatuses and methods for detection and/or analysis of volatile compounds contained in a sample or milieu, improvements of all components and steps are of interest.

In our PCT application WO 98/57141 is disclosed a system for the detection of an analyte in air. The collected air sample is transported to a first enrichment stage for enrichment of the analyte comprising a thermally regulated adsorption/desorption filter creating a non-laminar gas flow for adsorption of the analyte on the filter surfaces, encased in a housing having a gas inlet and a gas outlet connected to valves. The desorbed analyte from the filter is transported to a second enrichment stage, comprising a cold trap, for the further enrichment of the gaseous analyte by condensing the analyte, followed by extraction of the condensed material with a solvent, and collection of the solution enriched in analyte from the cold trap for transport to an analysis unit.

By transporting the desorbed analyte out of the filter housing with a weak gas flow to a cold trap for condensing the analyte on its walls and then rinsing the cold trap with a liquid to obtain a small liquid sample, some of the analyte is lost. It would be desirable to greatly reduce or eliminate the loss of analyte, i.e. loss of condensed volatile compounds, encountered in the prior art, particularly in cases where very small amounts of volatile compounds, in nanogram or picogram region, are to be detected or analyzed.

DESCRIPTION OF THE INVENTION

The present invention provides an improved apparatus and a method for concentrating and transferring volatile compounds contained in a solid, liquid or pre-concentrated gaseous sample placed on a detachable solid support into a liquid for subsequent delivery to an analysis unit for detection and/or analysis of one or several of the volatile compounds.

Thus, the present invention provides a system or an apparatus for concentrating and transferring volatile compounds contained in a solid, liquid or pre-concentrated gaseous sample placed on a detachable solid support into a liquid for subsequent delivery to an analysis unit for detection and/or analysis of one or several of the volatile compounds. The system or apparatus comprises a holder for the solid support, transporting means for transporting the holder from a solid support-receiving position to a heating position and back, the heating position being on top of a heatable plate, an enclosed space-creating arrangement comprising the heatable plate attached to a movable housing, the holder, the solid support, preferably a glass fiber based filter, a funnel on top of the solid support, and inside and on top of the funnel a chilled member, thermally regulated heating means inside the housing for heating the heatable plate to a temperature evaporating the volatile compounds which then are condensed on the chilled member, transporting means for transporting the chilled member from a cooler position to the inside and the top of the funnel as part of the enclosed space-creating arrangement and from the enclosed space-creating arrangement to a position where condensed compounds are removed from the chilled member into a liquid, and back to the cooler position.

The invention further provides a method for concentrating and transferring volatile compounds contained in a solid, liquid or pre-concentrated gaseous sample placed on a detachable solid support, preferably a glass fiber based filter, into a liquid for subsequent delivery to an analysis unit for detection and/or analysis of one or several of the volatile compounds. The method comprises the steps of positioning the solid support on a holder, transporting the holder to a position on top of a heatable plate, arranging an enclosed space comprising the holder, the heatable plate attached to a movable housing, the solid support, a funnel on top of the solid support, and inside and on top of the funnel a chilled member, heating the plate to evaporate the volatile compounds from the sample on the solid support and to condense the volatile compounds on the chilled member, and transporting the chilled member carrying the condensed volatile compounds from the enclosed space arrangement to a position where the condensed compounds are removed from the chilled member into a liquid.

The pre-concentration or transfer of a sample containing volatile compounds from a solid, liquid or gaseous milieu, particularly from air, onto a solid support, for example a filter of some type that is non-degradable at elevated temperatures, especially a glass fiber based filter, can be conducted in any suitable way. For example, the pre-concentration may be performed in some way known from the prior art, e.g. by vacuuming, by surface rubbing or by placing a sample onto the solid support. It is an advantage to have a detachable solid support, e.g. a filter, which is cheap and readily disposable so that a new sample can be placed on a new solid support, thus eliminating an otherwise necessary cleaning procedure.

The subsequent detection and/or analysis of one or several of the volatile compounds, originating from the sample and transferred into a liquid, can be performed in some way known from the prior art such as with e.g. an immunosensor, UV-cell, Gas chromatograph (GC), liquid chromatography columns etc.

The present invention is particularly useful in cases where it is advantageous, or even necessary, to concentrate a large sample of a milieu containing a small concentration of volatile compounds to be detected and/or analyzed.

The purpose of the method and apparatus of the invention is thus to concentrate preferably as much as possible, and transfer, volatile compounds contained in a solid, liquid or pre-concentrated gaseous sample placed on a solid support into a liquid, preferably to as small a volume of liquid as possible, in order to improve the sensitivity of a selected detection and/or analysis process.

It should be understood that the term "pre-concentrated gaseous sample" is used to describe the liquid or solid particles that are trapped on a solid surface, preferably a filter, when the gaseous milieu is passed by or through the surface.

An important element of this invention is a heat desorption step, which vaporizes the volatile compounds in the sample on the solid support. The created vapor is subsequently condensed onto a cold surface, i.e. a solid chilled member. The condensed material on the chilled member is subsequently flushed or rinsed with a liquid from the chilled member to form a preferably small liquid sample or is directly dissolved in a preferably small amount of solvent by immersion of the chilled member into a volume or stream of solvent, which then is transferred to a selected analysis unit.

The volatile compounds can be desorbed from a sample on the solid support into vapor form by either direct heating of a dry sample on the solid support or by wetting the sample on the solid support with a desired amount of e.g. water and steam distilling the substances off the solid support as a vapor mix. In both cases the vapor-phase is condensed on a chilled member.

The present invention is thus a link between pre-condensation or sampling of a desired milieu and an analysis unit used for detection and/or analysis of one or several volatile compounds from a preferably small liquid sample. Examples of volatile compounds that may be concentrated or purified and transferred from a sample on the solid support into a preferably small liquid sample with the apparatus and method of the present invention are low molecular weight substances, such as explosive substances (e.g. TNT, RDX), narcotics (e.g. cocaine, cannabis, heroine, amphetamines) and low-molecular weight biologically active compounds or biologically degraded compounds.

The invention will now be illustrated by the following description of embodiments, examples and the drawing, but it should be understood that the scope of protection is not limited to the disclosed details.

SHORT DESCRIPTION OF THE DRAWINGS

Figure 2:
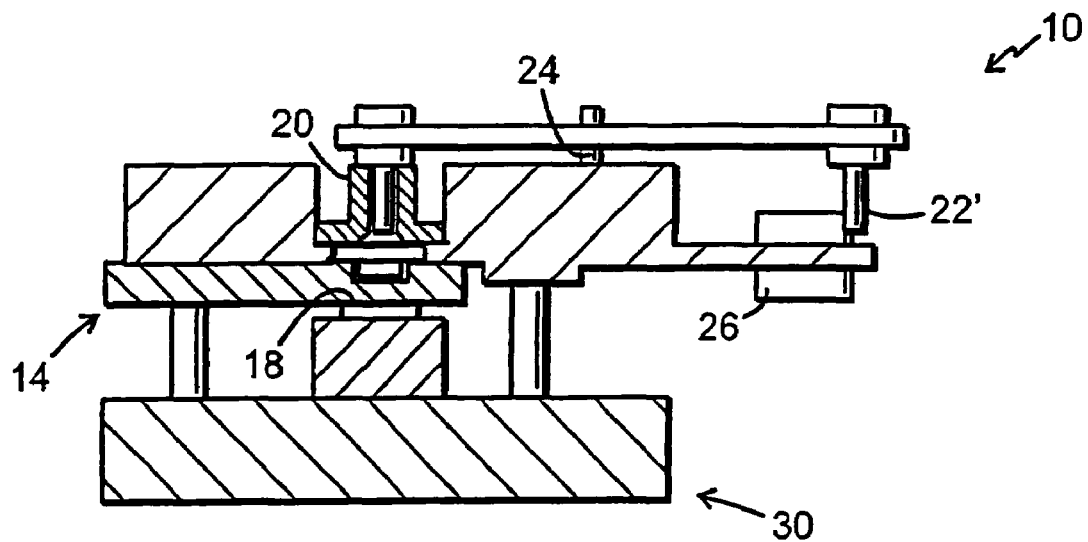

The drawings, FIG. 1 and FIG. 2, are schematic side views of elements comprised by an embodiment of the apparatus according to the invention.

DESCRIPTION OF EMBODIMENTS

A sample containing volatile compounds on a solid support, e.g. obtained from a pre-concentrator, is treated in the following way. Reference is made to the elements shown in the drawing.

The solid support 12 is positioned on a holder 14 in a transfer apparatus 10 of the invention. The shape and size of the holder 14 is adapted to receive the solid support 12. After the solid support is in place on the holder 14 the transporting means 16 transports or swings the holder 14 from its initial position to a heating position. The heating position is located above a heatable plate 18. A sample desorption area is formed as an enclosed space defined by the heatable plate 18 attached to a movable housing 30, the holder 14, the solid support 12, a funnel 20 located above the solid support, and a chilled member located within the funnel 20 and sealing the upper portion of the funnel 20.

In the desorption unit there is thermally regulated heating means inside the housing 30 for heating the heatable plate 18 to a temperature evaporating desired volatile compounds, but preferably not decomposing them. The vapors are condensed on the chilled member 22.

In a presently preferred embodiment, the metal plate is heated by a light source or an electrically heated foil inside the housing 30. Improved results are obtained when the solid support 12 is firmly attached to the metal plate 14. This may be facilitated by the use of a metal net or the like between the solid support 12 and the funnel 20 which then will be pressed against the outer edges of the solid support 12. The funnel shaft 21 has a form and a size that is adapted to receive the chilled member 22 at a short distance from the inner walls of the shaft.

The chilled member 22 is transported by the transporting means 24 from a cooler 26 position to the inside and the top of the funnel 20 as part of the enclosed space-creating arrangement, i.e. the desorption unit.

Thus, the chilled member 22 is cooled in a cooler 26 prior to being inserted into the shaft 21 of the funnel 20 in such a way that a small, air-tight space is formed between the funnel's inner walls and the chilled member 22. In the drawing, the chilled member 22 is illustrated by a rod, or in fact two rods 22,22' that can be used one after the other for transferring two subsequent samples.

When the solid support 12 swings into the position on the metal plate on top of the housing 30, the optional metal net, the funnel 20 and the chilled member 22 are rapidly brought into position to form the small air-tight space, and the metal plate is either already heated prior to receiving the solid support or is rapidly heated at this stage.

As the sample on the solid support 12 is heated, the volatile compounds are evaporated and subsequently condensed on the chilled member 22. Improved results are obtained if the funnel 20 is kept warm.

Transporting means 24 then lifts the chilled member carrying the condensed material up from the funnel shaft 21 and thus from the enclosed space-creating arrangement, i.e. desorption unit, and swings it to a position 28 where condensed compounds are removed from the chilled member 22 into a liquid.

At the position 28 the condensed compounds are removed from the chilled member 22 by flushing or rinsing with a liquid to form a preferably small liquid sample or are directly dissolved in a preferably minimal amount of solvent by immersion of the chilled member 22 into a volume of solvent or into a stream of solvent forming a plug in the stream, which then is transferred to the selected analysis unit.

For a new cycle, the transporting means 16 will transport the holder 14 back to the solid support-receiving position, and the transporting means 24 will transport the chilled member 22, optionally after cleaning, to the cooler position 26.

In an embodiment of the invention the heat source is placed into a vertically movable housing 30. The housing is e.g. cylindrical around the heat source. Between the heated filter 12 and the funnel 20, inside the funnel, there is a separate aluminum hood (not shown in the drawing) having a hole concentric with the funnel shaft 21 for receiving the tip of chilled member inside the enclosed space defined by the hood and the filter 12. There may also be some insulating space between the hood and the lower portion of the funnel 20. Such an arrangement keeps most of the heat within the hood whilst preventing the outer surface of the funnel 20 from becoming too warm.

When the solid support is in place over the heat source, the housing, the optional hood and the heat source are in one embodiment moved upwards. The solid support is thereby squeezed between the hood and a fixed cone or dome or funnel 20 located over the solid support, thus creating an inner seal close to the perimeter of the solid support. The contact surface of the solid support and the funnel is narrow and of the same shape as the solid support. It is positioned to be a small distance inside the outer edge of the solid support, maximizing the surface available on the solid support for desorption of the sample thereon. In this way there is a small, well defined volume created over the solid support.

The height of the cone or funnel should be such as to ensure that the appropriate volume is achieved. At this stage, a compatible liquid may be introduced into the defined volume before the heat source is activated or it may be left in a dry state. When the heat source is activated and the temperature increases the substances on the solid support are transferred either by the rapid vaporization of the liquid ("Steam" extraction) carrying the substances in the "steam" or by direct dry state vaporization or sublimation of the substances into the volume above the solid support and subsequently condensed on a cool surface (chilled member).

The cool surface or chilled member can have many topologies but as an example the process will be described using a rod. The rod is inserted through a hole at the top of the funnel and is preferably positioned such that the end part of the rod is close to the surface of the solid support. The rod has been cooled to a temperature below space temperature before it is inserted into the funnel. It might be necessary to cool down the rod also during the evaporation step to keep the rod temperature low enough to maximize the amount of condensed material on the rod. The cooling can be achieved a by a number of established techniques, such as by an active heat exchanging construction or just by heat transport from the tip to a larger cool bulk of the rod material itself. However, preferably it should be ensured that the temperature is as low as possible without condensing too much moisture from the surrounding air. The cold rod now acts as a condensation spot for the vaporized substances emerging from the warm solid support. The vaporized substances will condense on the first cold surface they meet, which according to the design of this apparatus will be a defined area of the rod. It is also important to keep the surrounding walls of the funnel warmer than the cold rod to prevent vapor from condensing there instead of on the rod.

In the disclosed embodiment of the apparatus of the invention, the heated vapors are deposited on the lowest part of the chilled area of the rod in near quantitative yields (see Table 1). Experiments have shown that no additional gas flow is necessary during the vaporization process, but the general construction of the apparatus and method of the invention does not exclude the use of a gas flow. However, a gas flow may decrease the yield of condensed material on the rod and is therefore not preferred. A gas flow probably disturbs the diffusion gradient, which is directed towards the cold surface. The flow of gas from the vaporization process is normally of sufficient volume and pressure to ensure rapid movement of the gases to the rod but under some conditions it may be necessary to assist the flow. This assistance will be provided naturally by the rapid vaporization of the liquid on the solid support (if used) or by an auxiliary source or by forced extraction of the gases from the cone, e.g. by vacuum.

In a presently preferred embodiment the top surface of the housing is flat or slightly convex to match the solid support and create as good and firm contact with its base as possible. From experiments it is evident that favorable results are obtained when a firm contact between the solid support and the hot surface is established. This is probably due to the avoiding of reverse diffusion of the substances through and/or behind the solid support. Heating the solid support directly by the heat source without the flat top surface of the housing and the firm contact between the heat source and solid support does not work satisfactorily, probably due to back diffusion in the apparatus.

In one embodiment of the invention the heat source is being used as a very fast heater for rapidly heating up the filter material to about 300° C. The heat transfer from the heat source to the solid support goes via the top surface of the housing. The temperature on the cold side of the solid support should preferably be at least 240° C. to allow all the substances tested so far to vaporize and condensate (sublimate) onto the tip of the rod. However, the temperature may in some cases be lower. Heating time is also a parameter of great importance. Preferably the solid support should not be heated more than for a maximum of 30 seconds in order not to degrade the substances, but also to keep the rod cold during the process. Best results so far are obtained when the top surface of the housing and the optional hood already has been pre-heated to a temperature of around 300° C. prior the contact with the solid support. In this way the overall heating time is reduced by almost a factor two.

The condensed volatile compounds on the tip of the rod, i.e. chilled member, can be removed and taken into solution by immersing the active area of the rod in a small volume of an appropriate solvent, such as water. This solution containing the volatile compounds can then be transferred to the analysis unit.

In an embodiment of the invention the rod can be moved to another position where it is washed with a suitable solvent prior to a new cycle.

In an automated embodiment of the invention the rod is moved by a step motor into the small device containing a small amount of solvent (e.g. 5–100 μl), such as water, after the sample has been deposited on the rod in the desorption part of the apparatus. The dimensions of this device should be such that the solvent forms a thin film rinsing the lower part of the rod, which contains most of the condensed substances.

When the substances have been transferred from the rod to a liquid, e.g. dissolved in a solvent, the transfer of the liquid or solution may be accomplished by opening a valve whereby the solution may e.g. enter into a liquid stream as a liquid plug, e.g. in a loop, and the liquid plug can be introduced into an analyzing unit e.g. an immuno-sensor, UV-cell, GC, liquid chromatography columns etc. The duration of the dissolution step typically does not take more than 5 seconds.

When the condensed volatile compounds have been dissolved from the rod, which, if necessary, is washed, the rod is returned to the cooler position followed by the position above the solid support holder which is in position for heating, and the process can be repeated. The rod can also be washed with additional water or solvent and re-chilled by a suitable technology on its way back to the collecting spot for a new cycle.

A reversible heat exchanger can be used both for cooling down the rod before and during the desorption process and heating it in the dissolution process to shorten the total desorption and dissolution processes. This could be advantageous in case the volatile compounds have poor solubility in the preferred solvent.

In an embodiment, the diameter of a solid support in the form of a glass fiber based filter is in the order of 2 cm. The dimensions of the cooled surface of the rod are a compromise between collecting as much substances as possible from the solid support and using as little liquid as possible when washing off the condensate. By using a rod diameter of about 6 mm the substances on the tip can be dissolved in a liquid volume of 50–100 microliters.

Another way of collecting the sample vapors in the desorption process from the solid support is to condense or dissolve the substances in a moving film of solvent. The solvent film moves over a collecting area positioned directly above the heated solid support at a suitable distance. The amount of water needed is about 25–100 μl in the above disclosed embodiment. The solvent film is very thin but of sufficient volume to dissolve the amount of substance needed for a positive identification in the analysis unit.

EXAMPLES OF USE OF THE METHOD AND APPARATUS OF THE INVENTION

Solid supports in the form of a glass fiber based filters of 2 cm diameter are spiked with various amounts (about 1–100 ng) of substances. The solid supports are placed on the metal plate in an apparatus of the invention, (c.f. the drawing) and the plate is heated to various temperatures during various desorption times (see Table 1). The materials on the rod are then dissolved using a small amount of water (50 microliters). The water is extracted with hexane and the hexane phase is analyzed by Gas Chromatography (GC). As can be seen in the table, the results showed almost a quantitative recovery of the materials on the solid supports.

TABLE 1

Yield of various substances in the small liquid samples after desorption from spiked solid supports.

| Substance | Desorption temp. | Desorption time | Desorption yield | Time for water dissolution | Yield water dissolution |
|---|---|---|---|---|---|
| Pyrene | 300° C. | 15 sec. | 100% | 30 sec. | 50% |
| Amphetamine | 250° C. | 10 sec. | 85% | 15 sec. | 100% |
| Cocaine | 300° C. | 15 sec. | 85% | 30 sec | 85% |
| Tetrahydrocannabinol (THC) | 350° C. | 30 sec. | 75% | 30 sec. | 75% |

In summary, the present invention provides an apparatus for transferring an optionally pre-concentrated sample containing volatile compounds from a solid support into a liquid for delivery to an analysis unit for detection and/or analysis of volatile compounds, comprising a holder for the solid support, transporting means for transporting the holder from a solid support-receiving position to a heating position, the heating position being on top of a heatable plate, an enclosed space creating arrangement comprising the heatable plate, the solid support, a funnel and inside the funnel a chilled member, transporting means transporting the chilled member from the enclosed space to a position where condensed compounds are removed from the chilled member into a liquid.

The invention further provides a method for transferring an optionally pre-concentrated sample containing volatile compounds from a solid support into a liquid for delivery to an analysis unit for detection and/or analysis of volatile compounds, comprising the steps of positioning the solid support on a holder, transporting the holder to a position on top of a heatable plate, arranging an enclosed space comprising the heatable plate, the solid support, a funnel and inside the funnel a chilled member, heating the plate to evaporate the sample from the solid support and to condense the volatile compounds on the chilled member, and transporting the chilled member from the enclosed space to a position where condensed compounds are removed from the chilled member into a liquid.

The invention claimed is:

1. An apparatus (10) for concentrating and transferring volatile compounds contained in a solid, liquid or pre-concentrated gaseous sample placed on a detachable solid support (12) into a liquid for subsequent delivery to an analysis unit for detection and/or analysis of one or several of the volatile compounds, which comprises
    a holder (14) for the solid support,
    transporting means (16) for transporting the holder (14) from a solid support-receiving position to a heating position and back, the heating position being on top of a heatable plate (18),
    an enclosed space-creating arrangement comprising the heatable plate (18) attached to a movable housing (30), the holder (14), the solid support (12), a funnel (20) on top of the solid support (12), and a chilled member (22) located within the funnel (20) and sealing the upper portion of the funnel (20)
    thermally regulated heating means inside the housing (30) for heating the heatable plate (18) to a temperature evaporating the volatile compounds which then are condensed on the chilled member (22),
    transporting means (24) for transporting the chilled member (22) from a cooler (26) position to the inside and the top of the funnel (20) as part of the enclosed space-creating arrangement and from the enclosed space-creating arrangement to a position (28) where condensed compounds are removed from the chilled member (22) into a liquid, and back to the cooler (26) position.

2. The apparatus (10) according to claim 1, wherein the detachable solid support (12) is a glass fiber based filter.

3. A method for concentrating and transferring volatile compounds contained in a solid, liquid or pre-concentrated gaseous sample placed on a detachable solid support into a liquid for subsequent delivery to an analysis unit for detection and/or analysis of one or several of the volatile compounds, which comprises the steps of
    positioning the solid support on a holder,
    transporting the holder to a position on top of a heatable plate, arranging an enclosed space comprising the holder, the heatable plate attached to a movable housing, the solid support, a funnel on top of the solid support, a chilled member located within the funnel and sealing the upper portion of the funnel,
    heating the plate to evaporate the volatile compounds from the sample on the solid support and to condense the volatile compounds on the chilled member, and
    transporting the chilled member carrying the condensed volatile compounds from the enclosed space arrangement to a position where the condensed compounds are removed from the chilled member into a liquid.

4. The method according to claim 3, wherein the detachable solid support is a glass fiber based filter.

* * * * *